United States Patent [19]

Klabunde

[11] 3,975,438

[45] Aug. 17, 1976

[54] PREPARATION OF o-IODOANILINE
[75] Inventor: Ulrich Klabunde, West Chester, Pa.
[73] Assignee: E. I. Du Pont de Nemours and Company, Wilmington, Del.
[22] Filed: May 8, 1974
[21] Appl. No.: 468,200

[52] U.S. Cl................................. 260/578; 252/426
[51] Int. Cl.$^2$......................................... C07C 87/60
[58] Field of Search................................... 260/578

[56] References Cited
OTHER PUBLICATIONS
Kovacic et al., Chem. Abstracts, 56, 15391i (1962).

Primary Examiner—D. Horwitz

[57] ABSTRACT

Described is the process of interconverting p-iodoaniline and o-iodoaniline, particularly converting p-iodoaniline to o-iodoaniline overall, by heating the former in the presence of aniline and, optionally, a mineral or organic acid.

16 Claims, No Drawings

PREPARATION OF O-IODOANILINE

BACKGROUND OF THE INVENTION

1. Field of the Invention

This invention relates to, and has as its principal object the provision of, an isomerization of p-iodoaniline to o-iodoaniline.

2. Prior Art

Despite extensive search, no reference to isomerization of haloanilines has been found.

RELATED CASE

This application is related to my copending application, Ser. No. 382,844, filed July 26, 1973, which deals with the synthesis of o-, m- and p-phenylenediamines and the intermediate amination of haloanilines. The o-iodoaniline employed in Ser. No. 382,844 for the preparation of o-phenylenediamine can be made by the method of the present application.

STATEMENT OF THE INVENTION

This invention comprises the process of rearranging p-iodoaniline and o-iodoaniline, particularly the former to the latter, wherein a mixture of p-iodoaniline or o-iodoaniline, aniline, and, optionally, a mineral or organic acid is heated at 150°–250°C for 10 minutes to 4 hours or more.

DESCRIPTION OF THE INVENTION

The reaction requires merely the addition of 1–100 parts by weight of aniline to one part of p- or o-iodoaniline. It is, however, conveniently carried out in a solvent selected from aniline, decalin, prehnitene, tribromobenzenes, especially 1,3,5-tribromobenzene, benzene, dimethylsulfoxide and hexamethyl phosphoramide. The amount of solvent, if one is employed, ranges from 1–100 parts by weight per part of p-iodoaniline or o-iodoaniline. Aniline is essential to the reaction and, for economic reasons and ease of separability, is the preferred solvent.

Lower boiling solvents such as water, benzene, and hexane can be used when the reaction is run under pressure.

The acids employed in the practice of this invention are acids which retain their acidic properties under the reaction conditions. They serve as catalysts for the rearrangement of p-iodoaniline. Preferred catalysts are hydroiodic acid or anilinium iodide. Only small amounts are essential, i.e., the ratio of acid to p-iodoaniline can range from 1:1 to 1:10,000 and is preferably about 1:1000 parts by weight.

The rearrangement of p-iodoaniline is generally carried out at the boiling point of the solvent which may range from about 150° to about 250°C, preferably at 180°–200°C, and most preferred at about 190°C.

The reaction times range from 10 minutes for the hydroiodic acid-catalyzed reaction to 4 hours or more.

These reactions are generally carried out at ambient pressure but may be run under mild autogenous pressure, e.g., up to about 20 atmospheres. The latter is inferred from Examples 4 and 5.

EMBODIMENTS OF THE INVENTION

The following examples are meant as nonlimiting illustrations of specific methods of practice of the invention.

In these examples, all quantities are given in parts by weight unless otherwise specified and temperatures are in degrees centigrade. The reaction products were determined by gas-liquid partition chromatography (glpc) in a 6 feet × ⅛ inch column packed with 3% Hi Eff 8BP on Chromosorb cyclohexane dimethanolsuccinate, (Applied Science Laboratories, Inc., State College, Pa.) at 200°C and a helium flow of 40 ml/minute. The injection and detection temperatures were 220°C and the sample size was 0.5 $\mu$l.

EXAMPLE 1

A. A mixture of 10.0 g of p-iodoaniline, 0.5 g of o-iodoaniline and 40 ml of aniline was heated to 190° and kept at this temperature for 1 hour. The dark purple solution was heated to 210°C for 30 minutes and ca. 25 ml of liquid was distilled. Analysis showed that the distillate consisted of only o-iodoaniline and aniline, and the pot residue consisted of aniline and iodoanilines in the ortho and para isomer ratio of 9:1, respectively.

B. When the experiment was carried out in the presence of sodium carbonate little, if any, isomerization was observed.

EXAMPLE 2

This example demonstrates the use of hydroiodic acid as a catalyst.

A. A mixture of 10 g of p-iodoaniline, 40 ml of aniline and 0.5 ml of concentrated aqueous hydroiodic acid was heated for 20 minutes at 188°. No color change was observed. Analysis showed aniline and o-iodoaniline.

B. When m-iodoaniline was treated similarly to p-iodoaniline, no isomerization occurred.

EXAMPLE 3

A mixture of 25 g of p-iodoaniline, 40 ml of aniline and 0.5 ml of 48% aqueous hydroiodic acid was refluxed under nitrogen for 2 hours. The violet solution was cooled and the aniline partly evaporated. The oil was dissolved in methylene chloride, extracted in turn with aqueous sodium hydroxide and water, then treated with Darco activated carbon. The solvent was evaporated, hexane added, and the mixture cooled to −40°C. The crystals that formed were collected and dried. The yield was 12.6 g (50% theoretical). The analysis (glpc) and infrared spectrum were identical to authentic o-iodoaniline.

| Anal. Calcd for $C_6H_6IN$: | | | |
|---|---|---|---|
| C, 32.91; | H, 2.76; | N, 6.40; | I, 57.90. |
| Found: C, 31.96; | H, 2.58; | N, 6.26; | I, 57.90 |
| 32.09 | 2,58 | 6.34 | 57.71 |

EXAMPLE 4

Each of fourteen 5-ml thick-walled, Pyrex ampoules was charged with 4 ml of a solution consisting of 15.17 g of p-iodoaniline, 7.20 g of 2-chlorobiphenyl, 101.64 g of freshly distilled aniline, and small amounts of the various acids listed in Table I. After briefly evacuating and sealing, the ampoules were kept in a 185° oil bath for 30 minutes. After cooling to 20°C, the dark purple contents of each ampoule were dissolved in 10 ml of methylene chloride, neutralized with 3 ml of 2N sodium hydroxide and the organic phase analyzed by glpc using the 2-chlorobiphenyl as the internal standard. The results are given as follows:

TABLE I

| Amounts of Acid | | Iodoaniline* | |
|---|---|---|---|
| | | % ortho | % para |
| None | None | 13 | 74 |
| 0.05 ml | 48% aq. HI | 71 | 23 |
| 0.1 ml | 48% aq. HI | 67 | 25 |
| 0.2 ml | 48% aq. HI | 69 | 22 |
| 0.5 ml | 48% aq. HI | 61 | 21 |
| 0.2 ml | Conc. HCl | 48 | 18 |
| 0.2 ml | Conc. HBr | 10 | 3 |
| 0.1 ml | Conc. $H_2SO_4$ | 66 | 30 |
| 0.2 ml | Water | 23 | 65 |
| 0.3 g | $C_6H_5NH_3Cl$ | 67 | 23 |
| 0.2 g | Toluenesulfonic acid | 71 | 25 |
| 0.2 g | $NH_4I$ | 76 | 23 |
| 0.2 g | $H_3PO_4$ | 46 | 19 |
| 0.2 ml | $CH_3CO_2H$ | 44 | 39 |

*Based on total amount of p-iodoaniline charged; remainder decomposed.

EXAMPLE 5

Table II lists the results for the experiments when the ortho isomer was used instead of the para isomer. The same conditions and relative quantities were used as described in Example 4.

TABLE II

| Amounts of Acid | | Iodoaniline* | |
|---|---|---|---|
| | | % ortho | % para |
| None | None | 99 | None |
| 0.2 ml | 48% aq. HI | 34 | 17 |
| 0.2 ml | $CH_3CO_2H$ | 96 | Trace |
| 0.2 ml | Conc. HCl | 10 | 2 |

*Based on the total amount of 0-iodoaniline charged; remainder decomposed.

The embodiments of the invention in which an exclusive property or privilege is claimed are as follows:

1. The process of converting p- to o-iodoaniline which comprises heating the former at about 150°–250°C. in the presence of 1–100 parts by weight of aniline per part of p-iodoaniline.
2. The process of claim 1 employing additionally an inorganic or organic acid which retains its acidic properties under the reaction conditions.
3. The process of claim 1 employing an additional inert solvent.
4. The process of claim 1 wherein o-iodoaniline is removed from the reaction mixture.
5. The process of claim 1 wherein the heating is conducted in the presence of a hydrogen halide.
6. The process of claim 1 wherein the heating is conducted in the presence of hydroiodic acid.
7. The process of claim 1 wherein the heating is conducted in the presence of hydrochloric acid.
8. The process of claim 1 wherein the heating is conducted in the presence of hydrobromic acid.
9. The process of claim 1 wherein the heating is conducted in the presence of sulfuric acid.
10. The process of claim 1 wherein the heating is conducted in the presence of toluenesulfonic acid.
11. The process of claim 1 wherein the heating is conducted in the presence of phosphoric acid.
12. The process of claim 1 wherein the heating is conducted in the presence of ammonium iodide.
13. The process of claim 1 wherein the heating is conducted in the presence of aniline hydrochloride.
14. The process of claim 1 wherein the heating is conducted in the presence of acetic acid.
15. The process of converting o- to p-iodoaniline which comprises heating the former at about 150°–250°C. in the presence of 1–100 parts by weight of aniline per part of o-iodoaniline and a hydrogen halide.
16. The process of claim 15 wherein the hydrogen halide is hydroiodic acid or hydrochloric acid.

* * * * *